United States Patent [19]

Iwakuma et al.

[11] Patent Number: 4,963,587
[45] Date of Patent: Oct. 16, 1990

[54] GLYCINE DERIVATIVE AND PHARMACEUTICAL PREPARATION THEREOF

[75] Inventors: Takeo Iwakuma, Ageo; Yasuo Sekine, Kawaguchi; Yasuhiko Sasaki; Katsuo Ikezawa, both of Urawa; Akio Odawara, Tokyo, all of Japan

[73] Assignee: Tanabe Seiyaku Co., Ltd., Osaka, Japan

[21] Appl. No.: 446,106

[22] Filed: Dec. 5, 1989

[30] Foreign Application Priority Data

Jan. 10, 1989 [JP] Japan ........................ 1-3548

[51] Int. Cl.⁵ .................... A61K 31/195; C07C 311/21
[52] U.S. Cl. .............................. 514/562; 514/534; 514/535; 560/10; 562/428
[58] Field of Search ............... 562/428; 514/535, 562, 514/534; 560/10

[56] References Cited

U.S. PATENT DOCUMENTS 4,748,271  3/1988  Meneghin ........................ 562/428
4,820,705  4/1989  Nickl et al. ..................... 562/428 X

OTHER PUBLICATIONS

Stegmeier et al., *Thrombosis Research*, 35, 379–395, (1984).

*Primary Examiner*—Werren B. Lone
*Assistant Examiner*—Vera C. Clarke
*Attorney, Agent, or Firm*—Birch, Stewart, Kolasch & Birch

[57] ABSTRACT

There are disclosed are glycine derivative of the formula:

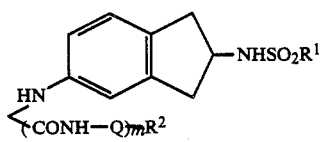

(wherein $R^1$ represents a substituted or unsubstituted phenyl group, $R^2$ represents a carboxyl group which may be protected, Q represents a lower alkylene group and m represents 0 or 1) or a pharmacologically acceptable salt thereof and a process for preparing the same.

8 Claims, No Drawings

GLYCINE DERIVATIVE AND PHARMACEUTICAL PREPARATION THEREOF

BACKGROUND OF THE INVENTION

This invention relates to novel indan derivatives having Thromboxane $A_2$ antagonistic activity and a process for preparing the same.

Thromboxane $A_2$ (hereinafter referred to as $TxA_2$) is a metabolite of arachidonic acid which exists widely in various organs of animals (e.g. liver, kidney, lung, brain, etc.). Said $TxA_2$ is known to show platelet aggregation activity and induces a variety of thromboses such as peripheral vascular thrombosis, pulmonary embolism, coronary artery thrombosis, myocardial infarction, transient ischemia, and the like. In this connection, 4-(2-benzenesulfonylaminoethyl)phenoxyacetic acid which shows $TxA_2$-antagonistic activity has been suggested to be useful for therapeutic treatment of these diseases (cf. Thrombosis Research, 35, pp. 379–395 (1984)).

SUMMARY OF THE INVENTION

The present invention concerns glycine derivatives represented by the following formula (I) or pharmacologically acceptable salts thereof which exhibit further excellent pharmaceutical activity than that of the above known compound.

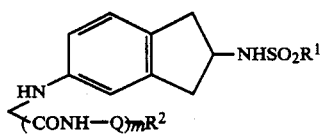
(I)

(wherein $R^1$ represents a substituted or unsubstituted phenyl group, $R^2$ represents a carboxyl group which may be protected, Q represents a lower alkylene group and m represents 0 or 1).

DESCRIPTION OF THE PREFERRED EMBODIMENTS

The glycine derivative (I) of the present invention and pharmacologically active salts thereof have excellent $TxA_2$ antagonistic activity, and are a pharmaceutical compound useful as a platelet aggregation inhibitor and a prophylactic and therapeutical agent of thrombosis, and also as a prophylactic and therapeutical agent of smooth muscle twitch of coronary and cerebral vessels and asthma, etc.

Specific examples of the glycine derivatives of the present invention may include the compounds of the formula (I), wherein $R^1$ is a phenyl group or a halogenophenyl group, $R^2$ is a free carboxyl group, or a carboxyl group protected with, for example, a lower alkyl group, a phenyl-lower alkyl group, a lower alkoxy-substituted phenyl-lower alkyl group, a nitro-substituted phenyl-lower alkyl group or benzhydryl group, etc., Q is a lower alkylene group and m is 0 or 1.

Among them, preferred compounds in therapy are those wherein $R^1$ is phenyl group or a halogenophenyl group, $R^2$ is a free carboxyl group or a lower alkoxycarbonyl group, Q is a lower alkylene group, and m is 0 or 1.

In the above specific examples, the lower alkyl group, the lower alkoxy group and the lower alkylene group mean an alkyl group, an alkoxy group and an alkylene group having 1 to 3 carbon atoms, respectively.

In the glycine derivative (I) of the present invention, two kinds of optical isomers based on one asymmetric carbon atom can exist, and the present invention is inclusive of either of these isomers and their mixtures.

The glycine derivative (I) of the present invention can be prepared by, for example, (1) subjecting a compound represented by the formula:

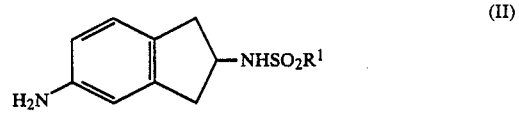
(II)

(wherein $R^1$ represents the same meaning as defined above) or a salt thereof and a compound of the formula:

$$XCH_2CONH-Q_mR^{21}$$ (III)

(wherein X represents a reactive residue, $R^{21}$ represents a carboxyl group which may be protected, Q and m have the same meanings as defined above) to condensation reaction, or (2) subjecting a compound of the formula:

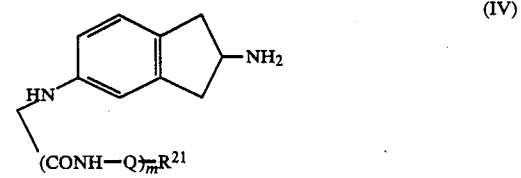
(IV)

(wherein $R^{21}$, Q and m have the same meanings as defined above) and a sulfonic acid compound of the formula:

$$R^1SO_3H$$ (V)

(wherein $R^1$ represents the same meaning as above) or a reactive derivative thereof to condensation reaction, and (3) when $R^{21}$ is a protected carboxyl group, removing, if desired, the protective group.

Also, of the glycine derivatives (I), the compound wherein m=1 can be also formed by subjecting a compound represented by the formula:

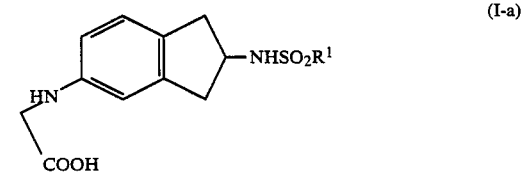
(I-a)

(wherein $R^1$ has the same meaning as defined above) or a reactive derivative thereof at the carboxyl group and an amine compound represented by the formula:

$$H_2N-Q-R^{21}$$ (VI)

(wherein $R^{21}$ and Q have the same meanings as defined above) or a salt thereof to condensation reaction, and when $R^{21}$ is a protected carboxyl group, removing, if desired, said protective group.

As the protective group of the carboxyl group in the starting compounds (III), (IV) and (VI), any of protective groups which can be easily removed by conventional treatment such as hydrolysis, reduction, solvolysis, acid treatment can be used, and examples of such protective groups may include lower alkyl groups, lower alkyl groups substituted with a substituted or unsubstituted phenyl group (e.g. benzyl group, p-methoxybenzyl group, p-nitrobenzyl group, etc.), benzhydryl group, etc. As the reactive residue X, for example, halogen atoms, lower alkylsulfonyloxy groups, substituted or unsubstituted phenylsulfonyloxy groups (e.g. benzenesulfonyloxy group, p-toluenesulfonyloxy group, etc.) can be suitably used. Further, as the reactive derivative of the compound (V), corresponding sulfonyl halide compounds can be preferably used.

The condensation reaction between the compound (II) and the compound (III) and the condensation reaction between the compound (IV) and the compound (V) or reactive derivative thereof can be practiced according to conventional methods. This reaction can be preferably practiced in the presence of a condensing agent. As the condensing agent, conventional ones such as a dehydrating agent (e.g. carbonyldiimidazole, dicyclohexylcarbodiimide, etc.) or an acid acceptor (e.g. alkali metal carbonate, alkali metal hydroxide, alkali metal bicarbonate, organic amine such as pyridine, tri-(lower alkyl)amine, etc.) can be suitably used. This reaction can be practiced in an appropriate solvent (acetone, chloroform, alkanol, methylene chloride, tetrahydrofuran, dimethyl sulfoxide, dimethylformamide, hexamethylphosphoric triamide, etc.). Also, this reaction can be practiced either under cooling or under heating.

The condensation reaction between the compound (I - a) or reactive derivative thereof at the carboxyl group and the amine compound (VI) can be practiced according to the conventional method either in the presence or absence of a condensing agent. As the reactive derivative at the carboxyl group of the compound (I - a), for example, corresponding acid halide or active ester is conveniently used. As the condensing agent, those conventionally used as exemplified in the condensation reaction as described above can be used. These condensation reactions can be all practiced in an appropriate solvent (e.g. tetrahydrofuran, methylene chloride), either under cooling or under heating.

When $R^{21}$ in the product thus obtained is a protected carboxyl group, said protective group may be removed, if desired, and removal of said protective group can be practiced according to the conventional methods such as hydrolysis, reduction, solvolysis and acid treatment.

The above reactions all proceed without racemization, and therefore, by use of an optically active isomer as the starting compound (II) or (IV), the glycine derivative (I) can be obtained as an optically active isomer.

The glycine derivative (I) or a salt thereof has, as described above, excellent $TxA_2$ antagonistic activity and therefore useful as platelet aggregation inhibitor, and can be used for therapy, relaxation and prophylaxis of various thromboses, embolisms., etc. such as cerebral thrombosis, coronary thrombosis, pulmonary thrombosis, pulmonary embolism, peripheral blood vessel embolism, thrombovasculitis, etc.

The glycine derivative (I) of the present invention can be used for medical use either in free form or in the form of pharmacologically acceptable salt thereof. As the pharmacologically acceptable salt, there may be included salts with inorganic or organic bases, for example, alkali metal salts such as sodium salt and potassium salt; alkaline earth metal salts such as calcium salt and magnesium salt; heavy metal salts such as zinc salt; ammonium salt; organic amine salts such as triethylamine salt, pyridine salt, ethanolamine salt and salt with basic amino acid; organic acid adition salts such as formate, oxalate, methanesulfonate and glucuronate.

The glycine derivative (I) or a salt thereof of the present invention can be administered either orally or parenterally, and can be also used in the conventional manner suitably as pharmaceutical preparation such as tablets, capsules, powders or injections.

The dose of the glycine derivative (I) or a salt thereof of the present invention, which may also differ depending on the method of administration, or the age, body weight, condition of the patient and the kind of the disease to be treated, may be generally about 0.01 to 50 mg/kg, particularly preferably 0.05 to 20 mg/kg, per day.

The starting compound (II) of the present invention is a novel compound, and can be prepared by nitrating 2-acetylaminoindan and then reducing, removing the acetyl group of 2-acetylamino-5-aminoindan thus obtained, followed by the condensation reaction with the compound (V). The starting compound (IV) is also a novel compound, and can be prepared by the condensation reaction between 2,5-diaminoindan and the compound (III).

EXPERIMENTAL EXAMPLE:

Inhibiting effect on arachidonic acid-induced pulmonary embolism (in vivo)

An aqueous carboxymethylcellulose (CMC) solution containing a test compound (20 ml/kg) was orally administered to ddy-male mice fasted overnight. Three hours later, arachidonic acid (125 mg/10 ml/kg) solution was injected to the tail vein of the mice to induce pulmonary embolism. The recovery time (minute) of locomotive activity of the mice was compared with that of the control group of mice to which a 0.25% aqueous CMC solution was administered instead of the test compound solution. The inhibiting effect of each test compound on arachidonic acid-induced pulmonary embolism was estimated in terms of a minimum effective dose, i.e., the dose required to shorten the recovery time by at least 15% as compared with the control group. The results are as shown in Table 1.

TABLE 1

| Inhibiting effect on arachidonic acid-induced pulmonary embolism (in vivo) | |
|---|---|
| Test compound[Note] | Minimum effective dose |
| (Compound of invention) | |
| Test Compound No. 1 | 0.3 |
| Test Compound No. 2 | 3 |
| Test Compound No. 3 | 3 |
| Control test compound | 30 |

Note
The names of the respective test compounds are as follows:

| Test compound No. | Compound name |
|---|---|
| 1 | {N-[2-(4-chlorophenyl)sulfonylaminoindan-5-yl]}glycine sodium salt |
| 2 | 3-{[[2-(4-chlorophenyl)sulfonylaminoindan-5-yl]amino]acetylamino}-n-propionic acid sodium salt |
| 3 | 4-{[[2-(4-chlorophenyl)sulfonylaminoindan-5-yl]amino]acetylamino}-n-butyric |

TABLE 1-continued

Control test compound: 4-(2-benzenesulfonylaminoethyl)-phenoxyacetic acid sodium salt

EXAMPLE 1

Into a solution of 0.5 g of 5-amino-2-(4-chlorophenyl)sulfonylaminoindan in 5 ml of hexamethylphosphoric triamide are added 0.2 g of sodium hydrogen carbonate and 0.25 g of methyl bromoacetate at 5 to 10° C., and the mixture is stirred at the same temperature for 4 hours. Water is added to the reaction mixture, followed by extraction with ethyl acetate. The extract is washed, dried and the solvent is evaporated. The residue is purified by separation through silica gel column chromatography (eluant: chloroform : ethyl acetate=7 : 3), and further recrystallized from ethyl acetate-n-hexane mixture to give 0.47 g of methyl N-[2-(4-chlorophenyl)sulfonylaminoindan-5-yl]glycinate.

Yield: 77%.
M.p.: 130–132° C. (decomposed) nujol.
IR $\nu_{max}$ (cm$^{-1}$): 3340, 3160, 1750

EXAMPLES 2 TO 6

Corresponding starting compounds were treated similarly as in Example 1 to give the compounds shown below in Table 2.

EXAMPLE 7

Into a solution of 0.46 g of methyl N-[2-(4-chlorophenyl)sulfonylaminoindan-5-yl]glycinate dissolved in 20 ml of a mixture of methanol-tetrahydrofuran (1:1) is added 1.22 ml of an aqueous 1 N sodium hydroxide solution, and the mixture is stirred at room temperature overnight, and further at 60° C. for 3 hours. After the reaction, the solvent is evaporated, and the residue is recrystallized from an isopropyl alcohol-water mixture to give 0.37 g of N-[2-(4-chlorophenyl)sulfonylaminoindan-5-yl]glycine sodium salt as colorless crystals.

Yield: 77%.
M.p.: 239–242° C. (decomposed) nujol.
IR $\nu_{max}$ (cm$^{-1}$): 3400, 3090, 1600.
Free carboxylic acid:
M.p.: 137–139° C. (decomposed) nujol.
IR $\nu_{max}$ (cm$^{-1}$): 3440, 3300, 3280, 1700, 1610

EXAMPLES 8 TO 12

Corresponding starting compounds are treated similarly as in Example 7 to give compounds as shown below in Table 3.

TABLE 2

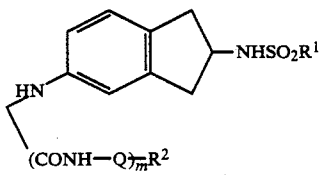

| Example No. | R$^1$ | R$^2$ | Q | m | Physical properties, etc. |
|---|---|---|---|---|---|
| 2 | phenyl | —COOCH$_2$CH$_3$ | — | 0 | M.p. 152–156° C (decomposed IR*$^1$: 3400, 3300, 1730 |
| 3 | phenyl | —COOCH$_3$ | —(CH$_2$)$_2$— | 1 | IR*$^2$: 3380, 3280, 1730, 1650 |
| 4 | 4-Cl-phenyl | —COOCH$_3$ | —(CH$_2$)$_2$— | 1 | M.p. 148–150° C. IR*$^1$: 3400, 3330, 1740, 1640 |
| 5 | phenyl | —COOCH$_3$ | —(CH$_2$)$_3$— | 1 | IR*$^2$: 3370, 3280, 1730, 1650 |
| 6 | 4-Cl-phenyl | —COOCH$_3$ | —(CH$_2$)$_3$— | 1 | M.p. 120–121° C. IR*$^1$: 3360, 3330, 3300, 3200, 1720, 1650 |

IR*$^1$: represents IR $\nu_{max}^{nujol}$ (cm$^{-1}$) (hereinafter the same)
IR*$^2$: represents IR $\nu_{max}^{liquid}$ (cm$^{-1}$) (hereinafter the same)

TABLE 3

| Example No. | R¹ | Q | m | Physical properties, etc |
|---|---|---|---|---|
| 8 | phenyl | — | 0 | M.p. 192–194° C. (decomposed) IR*¹: 3600–3200, 1600 Free carboxylic acid: IR*¹: 3280, 1720 |
| 9 | phenyl | —(CH₂)₂— | 1 | IR*¹: 3380–3240, 1650 Free carboxylic acid: IR*¹: 3360, 3260 1710, 1650 |
| 10 | 4-chlorophenyl | —(CH₂)₂— | 1 | IR*¹: 3400–3300, 1650 Free carboxylic acid: IR*²: 3380, 1720 |
| 11 | phenyl | —(CH₂)₃— | 1 | IR*¹: 3390–3230, 1650 Free carboxylic acid: IR*¹: 3360, 3270 1720, 1700 (sh) |
| 12 | 4-chlorophenyl | —(CH₂)₃— | 1 | IR*¹: 3280, 1650 Free carboxylic acid: IR*²: 3380, 1710 1650 |

(Preparation of starting compounds)

REFERENCE EXAMPLE 1

(1) 20.5 g of 2-acetylaminoindan is added gradually into 200 ml of fuming nitric acid under cooling. After the reaction, the reaction mixture is poured onto 100 g of ice, and the solvent is evaporated from the chloroform extract, and the residue is recrystallized from isopropyl alcohol to give 18.6 g of 2-acetylamino-5-nitroindan.

M.p.: 140–144° C.

(2) An ethanolic solution of 3.98 g of this product is catalytically reduced under ordinary temperature and pressure in the presence of 0.4 g of 10% palladium-charcoal. After the reaction, the catalyst is filtered off, and the filtrate is concentrated under reduced pressure. Ethyl acetate is added to the residue, and the crystals are obtained by filtration to give 3.04 g of 2-acetylamino-5-aminoindan.

M.p.: 154–156° C.

(3) This product (9.27 g) is added into 2 N hydrochloric acid, and the mixture is refluxed. After the reaction, the solvent is evaporated, and the residue is recrystallized from an isopropyl alcohol-water mixture to give 9.80 g of 2,5-diaminoindan dihydrochloride.

M.p.: >270° C.

(4) Into a solution of 4.0 g of this product in pyridine-methylene chloride is added 8.39 g of diazabicyclo[5.4.0]undeca-7-ene. Subsequently, under cooling, a methylene chloride solution of 3.36 g of benzenesulfonyl chloride is added dropwise with stirring. After the reaction, water is added, and the organic layer is separated, followed by evaporation of the solvent. The residue is crystallized from an ethanol-n-hexane mixture, purified through silica gel column chromatography, and recrystallized from an ethyl acetate-n-hexane mixture to give 2.98 g of 5-amino-2-benzenesulfonylaminoindan.

M.p.: 105–107° C.

REFERENCE EXAMPLE 2

2,5-Diaminoindan dihydrochloride and 4-chlorophenylsulfonyl chloride are treated similarly as in Reference example 1 - (4) to give 5-amino-2-(4-chlorophenyl)sulfonylaminoindan.

M.p.: 145–147° C. (recrystallized from chloroform-n-hexane).

What is claimed is:

1. A glycine derivative of the formula:

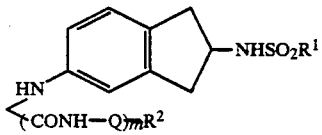

(I)

wherein R¹ represents a substituted or unsubstituted phenyl group, R² represents a carboxyl group which may be protected, Q represents a lower alkylene group and m represents 0 or 1 or a pharmacologically acceptable salt thereof.

2. A compound according to claim 1, wherein R¹ is a phenyl group or a halogenophenyl group.

3. A compound according to claim 2, wherein R² is a free carboxyl group or a lower alkoxycarbonyl group.

4. A compound according to claim 3, wherein R¹ is chlorophenyl group and R² is a free carboxyl group.

5. A compound according to claim 1, wherein said compound is selected from the group consisting of {N-[2-(4-chlorophenyl)sulfonylaminoindan-5-yl]}glycine, methyl N-[2-(4-chlorophenyl)sulfonylaminoindan-5-yl]glycinate, 3-{[[2-(4-chlorophenyl)sulfonylaminoindan-5-yl]amino]acetylamino}-n-propionic acid, 4-{[[2-(4-chlorophenyl)sulfonylaminoindan-5-yl]amino]acetylamino}-n-butyric acid, and a pharmacologically acceptable salt thereof.

6. A pharmaceutical composition exhibiting platelet aggregation inhibiting activity which comprises a therapeutically effective amount of the compound in claim 1 or a pharmaceutically acceptable salt thereof in admixture with a pharmaceutically acceptable carrier or diluent.

7. A method for the treatment or prophylaxis of a thrombotic disease in a warm-blooded animal in need thereof which comprises administering an effective amount of the compound as set forth in claim 1 to the warm-blooded animal.

8. A compound according to claim 1, wherein R¹ is a phenyl group or a halophenyl group, R² is a free carboxyl group or a lower alkoxycarbonyl group, Q is a lower alkylene group and m is 0 or 1.

* * * * *